(12) United States Patent
Johnson et al.

(10) Patent No.: US 6,372,885 B1
(45) Date of Patent: Apr. 16, 2002

(54) SOLID-PHASE TECHNOLOGY FOR THE PREPARATION OF AMIDES

(75) Inventors: Tony Johnson, Cambs; Martin Quibell, Cambridge, both of (GB)

(73) Assignee: Peptide Therapeutics Limited, Cambridge (GB)

( * ) Notice: Subject to any disclaimer, the term of this patent is extended or adjusted under 35 U.S.C. 154(b) by 0 days.

(21) Appl. No.: 09/284,852

(22) PCT Filed: Oct. 22, 1997

(86) PCT No.: PCT/GB97/02914

§ 371 Date: May 20, 1999

§ 102(e) Date: May 20, 1999

(87) PCT Pub. No.: WO98/17628

PCT Pub. Date: Apr. 30, 1998

(30) Foreign Application Priority Data

Oct. 22, 1996 (GB) .............................................. 9621985

(51) Int. Cl.[7] .......................... A61K 31/00; C07K 5/00; G01N 33/53; G01N 33/543; C07C 233/00
(52) U.S. Cl. ........................ 530/334; 435/7.1; 435/7.2; 435/DIG. 49; 436/501; 436/518; 530/333; 530/335; 544/168; 564/152; 564/155; 564/158; 564/161; 564/163; 564/168
(58) Field of Search .................... 435/7.1, 7.2, DIG. 49; 436/501, 518; 530/333, 334, 335; 564/152, 155, 158, 161, 163, 168; 544/168

(56) References Cited

FOREIGN PATENT DOCUMENTS

| EP | 0 519 748 A2 | 12/1992 |
|---|---|---|
| EP | 0 528 487 A2 | 2/1993 |
| EP | 0 533 226 A2 | 3/1993 |
| EP | 0 547 699 A1 | 6/1993 |
| WO | 92/18144 | 10/1992 |
| WO | 93/14777 | 8/1993 |
| WO | 93/16710 | 9/1993 |
| WO | 96/00378 | 1/1996 |
| WO | 96/30392 | 10/1996 |

OTHER PUBLICATIONS

Greene, T.W. and Wuts, P. G. Protective Groups in Organic Synthesis, 2nd Ed. New York: John Wiley & Sons, Inc. 1991, pp. 10–87.*
Hermkens et al. Tetrahedron, vol. 52, No. 13, pp. 4527–4554, Mar. 1996.*
Mandal et al, "Role of the Central Metal Ion and Ligand . . . ," Bioconjugate Chem., vol. 8, pp. 798–812 (1997).
Songster et al, "Acid–labile handles for Fmoc . . . ," Letters in Peptide Science, vol. 2, pp. 265–270 (1995).
Offer et al, "On–resin solid–phase synthesis of asparagine . . . ," J. Chem. Soc., Perkin Trans. 1, pp. 175–182 (1995).

Johnson et al, "Backbone protection and its application to the synthesis . . . ," J. Chem. Soc., Perkin Trans. 1, pp. 719–728 (1995).
Chemical Abstracts 99:28006, "Antitumor formulations containing . . . ".
Calmes et al, "Use of a new sonically cleavable . . . ," 6129 Int'l. Journal of Peptide & Protein Research, vol. 44, No. 11, pp. 58–59 (1994).
Ostresh et al, "Peptide Librarise: Determination of Relative Reaction . . . ," pp. 1681–1689 (1994).
Pinilla et al, "Rapid Identification of High Affinity . . . ," BioTechniques, vol. 13, No. 6, pp. 901–905 (1992).
Wallace et al, "A Multimeric Synthetic Peptide . . . ," Peptide Research, vol. 7, No. 1, pp. 27–31 (1994).
Owens et al, "The Rapid Identification of HIV Protease Inhibitors . . . ," Biochem. and Biophys. Research Communications, vol. 181, No. 1, pp. 402–408 (1991).
Pinilla et al, "Investigation of antigen–antibody interactoins using a . . . ," Biochem. J., vol. 301, pp. 847–853 (1994).

(List continued on next page.)

Primary Examiner—Jyothsna Venkat
Assistant Examiner—Maurie E. Garcia
(74) Attorney, Agent, or Firm—Nixon & Vanderhye

(57) ABSTRACT

Method for preparing a combinatorial chemistry library of compounds of the formula R1—C(=O)—NH—R2, wherein R1 and R2 are as defined in the specification, which comprises acylating a combinatorial chemistry intermediate of the formula 1A

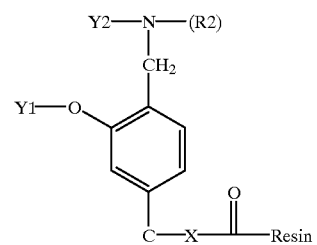

wherein Y1, Y2, X, n, R1 and R2 are as defined in the specification to produce a compound of the formula

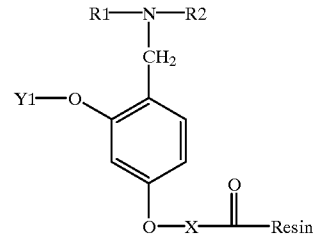

wherein Y1, R1, R2 and X are as defined in the specification, followed by acidolytic cleavage of the resin bound linker to release the compound of the formula R1—C(=O)—NH—R2.

6 Claims, No Drawings

OTHER PUBLICATIONS

Hart et al, "Preparation and Use of Combinatorial Libraries . . . ," Peptide.

Eichler et al, "Identification of Substrate Analog Trypsin . . . ," Biochemistry, vol. 32, pp. 11035–11041 (1993).

Dooley et al, "The Use of Positional Scanning Synthetic . . . ," Life Sciences, vol. 52, pp. 1509–1517 (1993).

Pinilla et al, "Versatility of Positional Scanning . . . ," Drug Development Research, vol. 33, pp. 133–145 (1994).

* cited by examiner

SOLID-PHASE TECHNOLOGY FOR THE PREPARATION OF AMIDES

This application is 471 of PCT/GB97/02914 filed Oct. 22, 1997.

INTRODUCTION

With the identification of a molecular target associated with a particular disorder, the medicinal chemist works towards a drug molecule which intervenes in a particular pathway preventing progression of the disorder. The route towards a potent and selective drug proceeds through a number of stages. For example, when faced with an aberrant protease the protease is initially isolated and purified. An assay for activity is then established and a molecule that inhibits the proteolytic activity developed and systematically refined to provide a drug candidate with the desired potency and selectivity. This route is time consuming and expensive, thus tools which expedite a part of the whole process of drug development are extremely attractive commercially.

Combinatorial chemistry techniques, which are methods for the parallel preparation of many molecules compared to traditional single serial techniques, have the potential to play a pivotal role in the design and development of drug-like molecules. Co-pending UK Patent Application No. 9608457.9 describes a combinatorial library technology which has been developed as a tool to accelerate the development of inhibitors of proteolytic enzymes. A protease is screened against a large addressable library of potential protease substrates, swiftly providing an assay for proteolytic activity based upon internally quenched fluorescence. Along with the establishment of a sensitive assay, a wealth of substrate structure-activity data is gathered which may be used in the design oil an inhibitor. (Where legally permissible GB 9608457.5 is incorporated herein by reference).

A large proportion of the molecules that have previously or are currently being developed as protease inhibitors or in fact many other drug classes can be represented by the simple general formula (1)

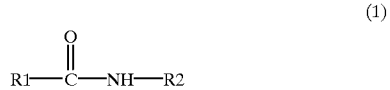

(1)

Two fundamental approaches towards the preparation of molecules such as (1) are available. Traditionally, solution phase based serial chemistries have been used to provide single molecules. Recently these serial solution chemistries have begun to develop into parallel combinatorial methods in which R1 and/or R2 are varied providing 10's–100's of molecules swiftly. Over the last 30 years, the expedient methods of solid phase chemistry have also developed. Solid phase methods have the potential to rapidly produce many thousands of molecules. However, the ease with which different classes of the general formula (1) can be varied in both R1 and R2 simultaneously depends upon the specific nature and functionality of R1 and R2. For example, when R1 and R2 are standard amino acid structures, providing the general class 'peptides', solid phase methods have developed sufficiently to provide single peptides or thousands/millions of peptides in a combinatorial library format with relative ease.

Generally, protease inhibitors are designed with recognition elements from the substrate (i. e. R1), and are often coupled with a chemical moiety (i.e. R2) which interacts with the protease to inhibit proteolytic activity.

The combinatorial protease inhibitor library assay technique of GB 9608457.9 provides an example of parallel preparation of molecules (1) in which there is flexible combinatorial variation of R1. Chosen specific effective examples of (1) from the combinatorial library must then be assayed for effectiveness as a protease inhibitor with individually serially varied moieties R2.

The solid phase techniques currently available are not sufficiently developed to enable flexible combinatorial variation of both R1 and R2 in the majority of classes of (1), even in a simple serial manner as single entities, let alone as combinatorial libraries. Thus a solid phase combinatorial library method, enabling the rapid preparation of hundreds or thousands of compounds across many classes of (1) would potentially be extremely attractive for physicochemical/structure-activity profiles in the development of drug candidates. Additionally, such a methodology would expedite the transformation of R1 substrate data derived from the library described in GB 9608457.9 into an effective inhibitor, a process which is currently time consuming using solution based techniques.

It will readily be appreciated by those skilled in the art that a general solid phase combinatorial route to molecules of structure (1) would not be restricted to the development of protease inhibitors. Any type of interaction e.g. receptor agonists, antagonists for which molecules of type (1) exhibit activity may be developed in a combinatorial manner. Here, a novel solid-phase methodology is described allowing the flexible variation of R1 and R2 in many classes of general structure (1), and allowing a combinatorial approach leading to parallel preparation of many molecules.

Background Chemistry—The Current Problem

Solid phase based synthesis utilise cross-linked polymers (a resin support) which is functionalised with a chemically reactive unit (a linker). A functional group (carboxylic acid, amine, hydroxyl, sulphydryl etc) from an initial intermediate of the final desired compound is reversibly and covalently attached to the resin through the linker. Sequential chemical transformations of this now resin-bound intermediate to the final compound are then performed. At each stage, excess and spent reagents are removed from the growing resin-bound product by simple filtration and washing—this being the overriding factor providing expedient synthesis compared to solution based synthesis. As a final step, the fully assembled product is released from the solid support by cleavage of the covalent bond between the linker and product functional group.

To date, peptides provide the vast majority of compounds of general formula (1) prepared. Traditional solid phase peptide synthesis utilises a linker derivatised resin support to which the Cα carboxyl of the C-terminal residue is covalently attached. The desired sequence is sequentially assembled (using individual elements at each stage to give a single final product or using mixtures of elements at each stage to give a mixture or 'library' of final products). Then the product is released into solution by cleavage of the C-terminal residue—linker bond. This provides the free C-terminal carboxylic acid. To provide alternative C-terminal functionalities different linkers have been developed. However virtually all linkers described to date release a functional group (carboxylic acid, amine, hydroxyl, sulphydryl etc) present in the final product. Thus an obvious problem arises if the desired compound is devoid of one of the above functionalities, as many classes of (1) are. For example peptidyl acyloxymethyl ketones, of the general formula (2), a potent class of inhibitor of the cysteinyl protease Der p I, a major allergen of the house dust mite, are a member of the general class (1), but contain no obvious functional group to which a linker can attach an intermediate to a resin. Therefore current solid phase techniques cannot prepare potential drug candidates of the general structure (2) as single discrete compounds let alone defined libraries of analogues.

(2)

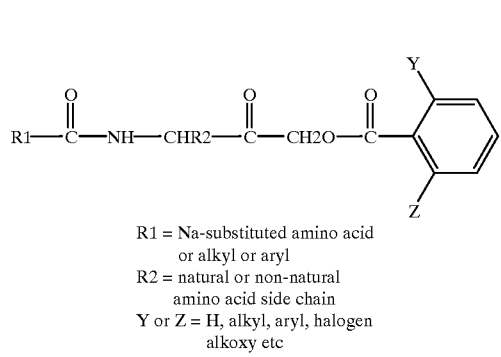

R1 = Nα-substituted amino acid or alkyl or aryl
R2 = natural or non-natural amino acid side chain
Y or Z = H, alkyl, aryl, halogen alkoxy etc Co-pending PCT Application No. PCT/GB96/01707 describes in more detail the cysteinyl protease Der p I inhibitors (2) and their preparation. (Where legally permissible PCT/GB96/01707 is incorporated herein by reference). A Novel Solid—Phase Based Solution
i) Strategy The only functional element that is always present in (1) is the secondary amide group (3). Thus, the attachment of initial intermediates of general formula (1) through the conserved secondary amide group to a resin support provides a unique route to any class of (1). Following subsequent solid phase assembly of the desired compound/s, the covalent bond between the linker and now tertiary amide is cleaved to regenerate the conserved secondary amide (3). Scheme 1 below. During the sequential chemical transformations leading to the final secondary

SCHEME 1

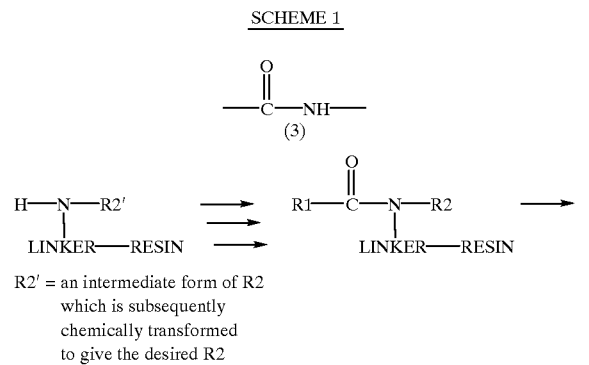

R2' = an intermediate form of R2 which is subsequently chemically transformed to give the desired R2 amide product, one has two options. Coupling reactions (the addition of a new chemical moiety providing a part of the final product) maybe performed using single building blocks, leading to a single final product. Alternatively, each coupling stage may be performed using chemical mixtures, providing a combinatorial library of final products in which both R1 and R2 have been varied. This latter route greatly expands the number and range of drug-like molecules that may be accessed in an overall drug discovery programme.

ii) Chemistry

The vast majority of solid phase synthesis described over the last decade uses side-chain functional group protection which is removed by acidolytic cleavage together with Nα-protection removed by base. The wide range of commercially available building blocks are thus based upon this Scheme. A popular strategy in solid phase synthesis is, as a final synthetic step, the concomitant removal of side-chain protection along with product-linker cleavage. Thus, many linkers described in the literature are cleaved from the product by acidolytic treatment. A further desirable feature of a linker is the ability to readily derivatise (i.e. addition of R1—CO— in Scheme 1) with a wide range of reagents. An ideal linker for Scheme 1 should therefore encompass all or the above properties. However, to date, no such linker has been described to our knowledge.

There are a number of backbone amide protecting groups which generate amides upon acidolytic treatment described in the literature. Johnson, Quibell and Sheppard have described the development of a backbone amide protection system outlined in Scheme 2.

SCHEME 2

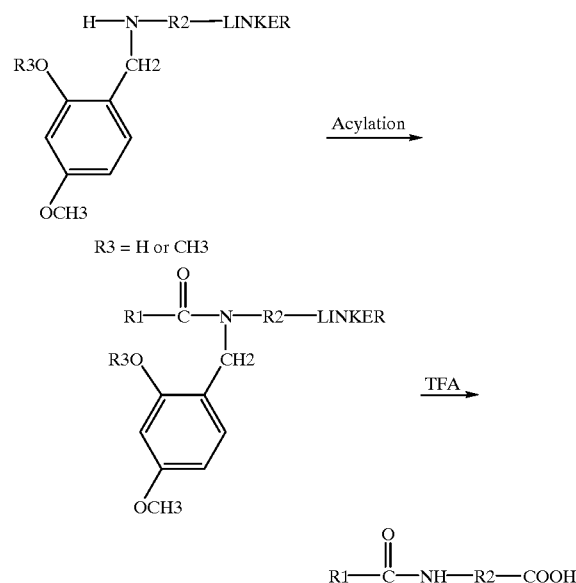

This system (not a linker in its own right) was designed to protect the backbone amide of a peptide (previously attached to the resin through a C-terminal residue-linker moiety) during synthesis. Following completion of peptide assembly, the group was removed as a final step along with side-chain deprotection and peptide-linker cleavage by trifluoroacetic acid (TFA). It was found that in Scheme 2 the use of a 2-hydroxyl (R3=H) rather than a 2-methoxy (R3=OCH3) group allowed the subsequent acylation to be performed with a wide range of reagents, through an acyl transfer mechanism. In contrast, the 2-methoxy derivatised system cannot undergo the acyl transfer reaction and was found to have a very limited applicability.

The group of Barany have recently described a backbone amide linker shown in Scheme 3.

SCHEME 3

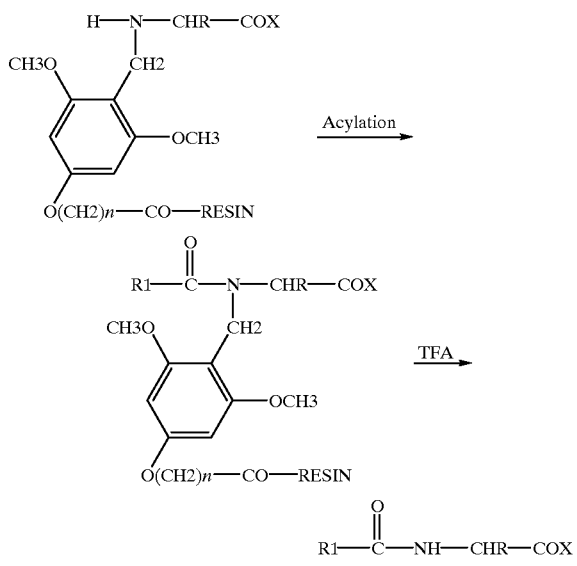

This linker does not contain the acyl transfer option during acylation and is therefore not of general applicability.

The present invention provides a combination of the elements described in Schemes 2 and 3 and leads to the backbone amide linker system shown in Scheme 4. This now contains an acyl transfer element (i.e. —OY=2-hydroxyl moiety along with the correct chemical properties of the backbone amide linker making the system compatible with a wide body of commercially available reagents. The linker outlined in Scheme 4 provides us the necessary chemistry to achieve the general goal described in Scheme 1, this being the flexible combinatorial preparation of many libraries of different classes of drug-like molecules with general formula (1), having both R1 and R2 variable simultaneously.

SCHEME 4

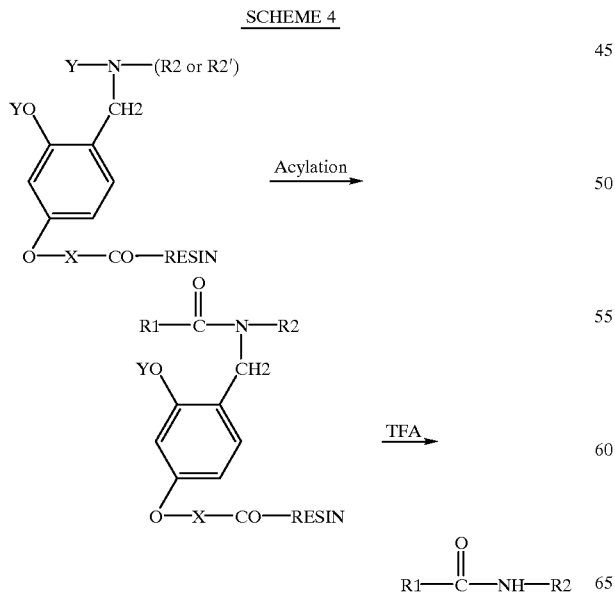

and wherein
X is

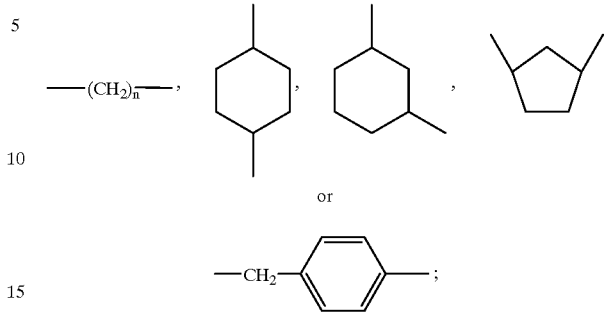

Y is H or a side chain functional group protective moiety such as Fmoc;

R2$^1$ is an intermediate form of R2 which is subsequently chemically transformed to give the desired R2; and n is between 2 and 12, preferably 4.

The present invention provides in a first aspect an intermediate compound of general formula (A)

(A)

for use in a method of preparation of a compound of general formula (1)

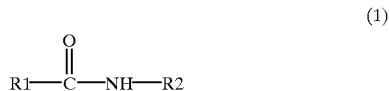

(1)

wherein the linker moiety has the general formula (B)

(B)

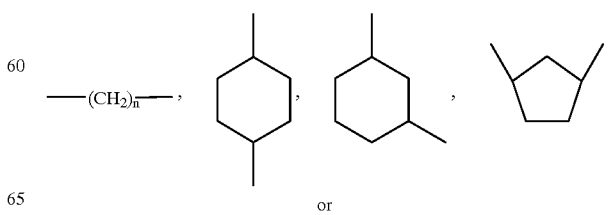

and wherein:
X is

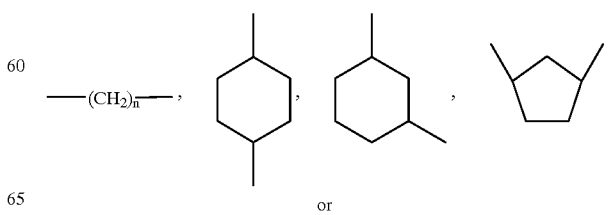

-continued

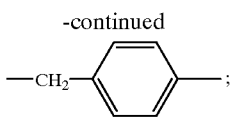

Y is H or a side chain functional group protective moiety such as Fmoc;

R2$^1$ is an intermediate form of R2 which is subsequently chemically transformed to give the desired R2; and n is between 2 and 12, preferably 4.

In a second aspect the present invention provides an intermediate compound of general formula (C)

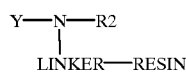

(C)

wherein the linker moiety has the general formula (B)

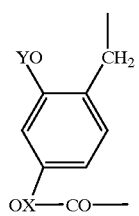

(B)

and wherein:

X is

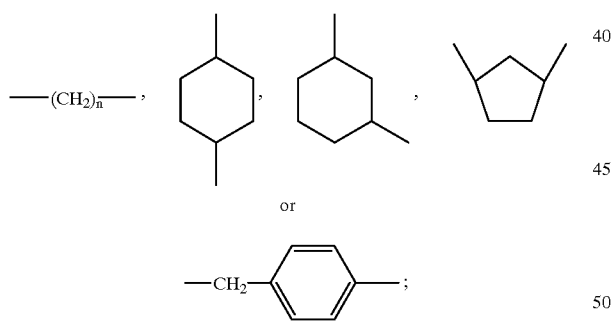

Y is H or a side chain functional group protective moiety such as Fmoc;

n is between 2 and 12, preferably 4.

The present invention also provides an acyl derivative of an intermediate compound shown above having the general formula (D) (D$^1$)

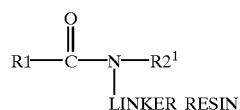

(D$^1$)

-continued

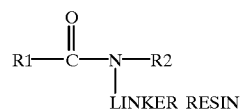

(D)

The present invention also provides a compound of general formula (E)

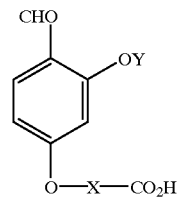

(E)

for use in a method of preparation of an intermediate compound shown above.

The present invention also provides compounds of general formula (F) and (G)

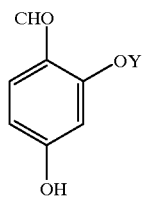

(F)

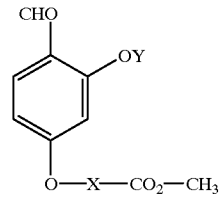

(G)

for use in a method of preparation of a compound (E)

According to the present invention there is provided a method for the preparation of a compound of general formula (1) using an intermediate compound shown above which method includes the following steps:

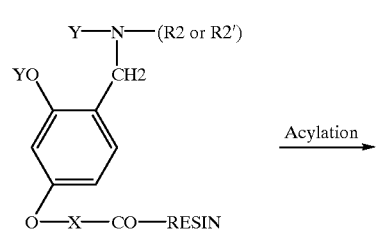

-continued

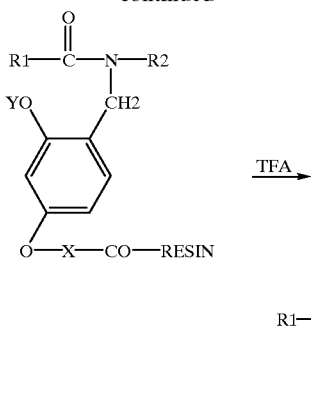

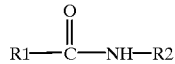

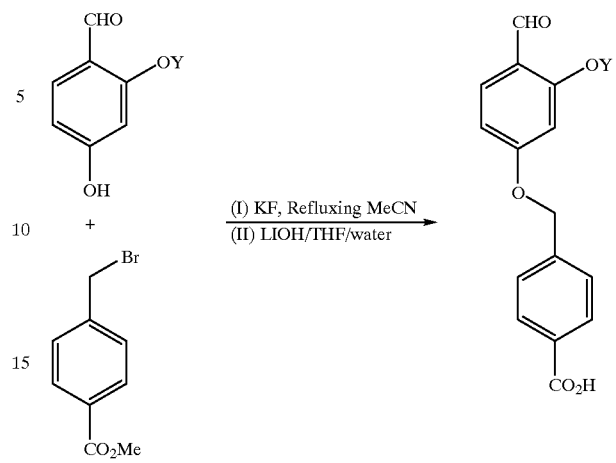

The invention further provides a method for the preparation of a compound of, general formula (E) which method includes the following steps:

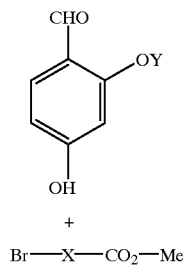

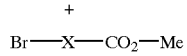

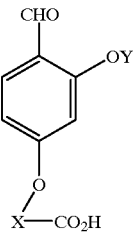

The invention also provides compounds which are the products of the methods above.

Also the invention provides for the use of compounds of the invention in a method for the preparation of a combinatorial library of compounds of general formula (1) in which both R1 and R2 are variable.

Preferably in compounds of formula (B) (E) and (G); Y=H and X=$(CH_2)_n$ where n=4.

EXAMPLE USE OF THE NOVEL TECHNOLOGY

Preparation of a Linker

One example of a preparative method for a linker moiety according to the invention is illustrated below:

A second example of a preparative method for a linker moiety according to the invention is illustrated below:

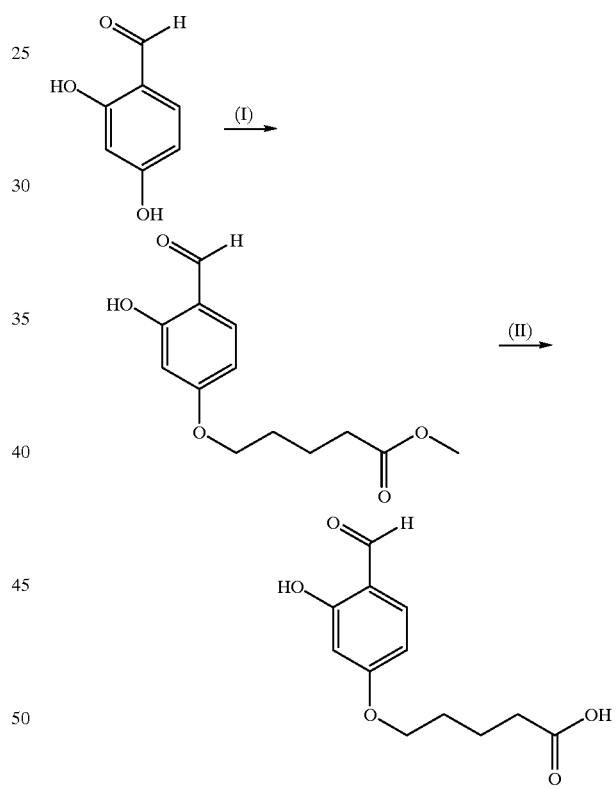

(I) 2,4-Dihydroxybenzaldehyde (mw.138.1, 50 g, 0.36 mol) and spray-dried potassium fluoride (mw.58.1, 41.8 g, 0.72 mol) were stirred vigorously at 60° C. for 20 mins in anhydrous acetonitrile (750 mL); methyl-5-bromovalerate (mw.195.1, 140.4 g, 0.72 mol) was added in one portion and the mixture brought to gentle reflux for 5 hours. The reaction was allowed to cool to room temperature and the solvent removed in vacuo; the residue was partitioned between water (500 mL) and ethyl acetate (250 mL), the aqueous washed twice more with ethyl acetate (2×150 mL) and the combined organic back-washed with water, dried over anhydrous magnesium sulphate, filtered and evaporated to dryness. The resulting red oil was dissolved in methyl tert-butyl ether (150 mL), heptane (100 mL) added and the product allowed to crystallize out as an off-white solid (mw.252.3, 37.3 g, 0.148 mol, 41% yield); $^1$H NMR (CDCl$_3$)δ11.44 (1H, s), 9.69 (1H, s), 7.41 (1H, d, J=8.6 Hz), 6.51 (1H, dd, J=8.6, 2.2 Hz), 6.39 (1H, d, J=2.2 Hz), 4.02 (2H, t, J=5.8 Hz), 3.66 (3H, s), 2.44 (2H, t, J=7.0 Hz), 1.83 (4H, m); IR (film) 1735 cm$^1$; mp. 62–65° C.; ESMS m/z 253 (M$^+$+1); HPLC rt. 15.4 min, 10–90% B in A, A=0.1% aq. TFA, B=10% A in MeCN, linear gradient 25 min, 1.5 mL/min, column=Vydac protein C4, 4.6×250 mm, 5 μparticle size.

(II) The product of step (I), 5-(4-Formyl-3-hydroxyphenoxy)pentanoic acid methyl ester (mw. 252.3 37 g, 0.147 mol) was dissolved in THF (1200 mL) and stirred vigorously at room temperature. To this solution was added lithium hydroxide (mw.41.96, 18.5 g, 0.441 mol) dissolved in water (600 mL) and the mixture stirred for 4 hours. The solvent was reduced in vacuo and the resulting oily residue diluted with water (200 mL), washed twice with methyl tert-butyl ether (2×500 mL) acidified carefully to pH 2 with conc. HCl (vigorous stirring) and extracted with ethyl acetate (4×300 mL). The combined ethyl acetate was dried over anhydrous magnesium sulphate, filtered and evaporated to dryness to give the product as a white solid (mw.238.2, 32 1 g, 0.135 mol, 92% yield); $^1$H NMR (CDCl$_3$)δ11.26 (2H, br.s), 9,69 (1H, s), 7,41 (1H, d, J=8.6 Hz), 6.51 (1H, dd, J=8.6, 2.2 Hz), 6.40 (1H, d, J=2.2 Hz), 4.02 (2H, t, J=5.9 Hz), 2.44 (2H, t, J=7.0 Hz), 1.84 (4H, m); IR (film) 1697, 1626 cm$^1$; mp, 88.6–89.1° C.; ESMS m/z 239 (M$^+$+1), HPLC rt. 14.3 min, 10–90% B in A, A=0.1% aq. TFA, B=10% A in MeCN, linear gradient 25 min, 1.5 mL/min, column=Vydac protein C4, 4.6×250 mm, 5 μ particle size.

Combinatorial Library of Peptidyl Acyloxymethyl Ketones

Scheme 5 illustrates a potential use of the new solid phase combinatorial technology for the preparation of a library of peptidyl acyloxymethyl ketones as potential inhibitors of the cysteinyl protease Der p I.

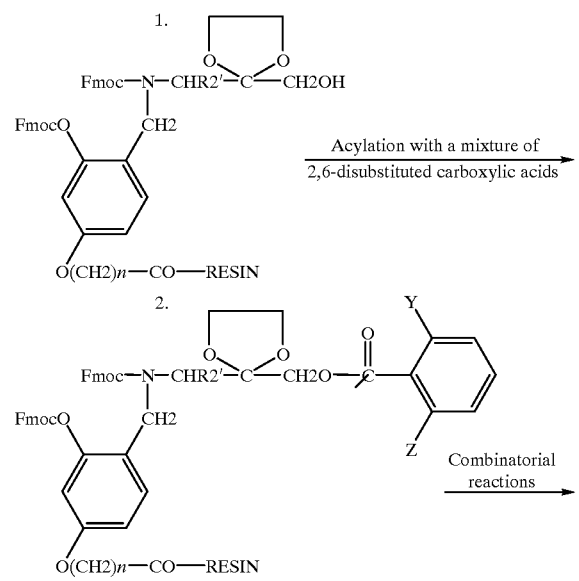

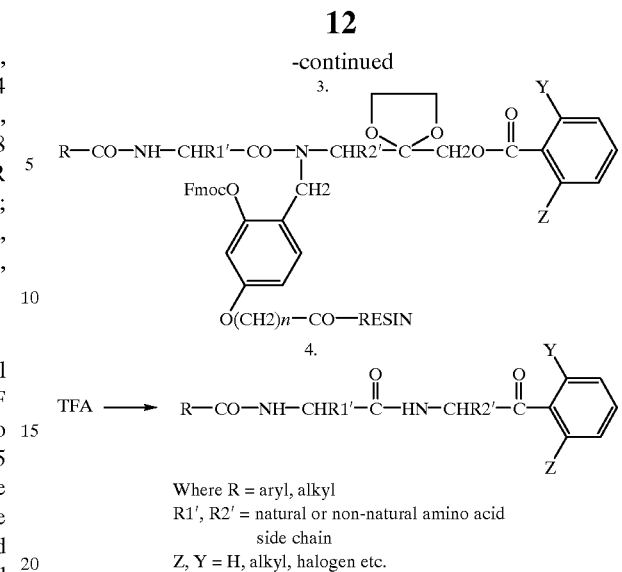

Where R = aryl, alkyl
R1', R2' = natural or non-natural amino acid side chain
Z, Y = H, alkyl, halogen etc.

Currently, there are approximately 200 commercially available Fmoc—NH—CHR1'—COOH building blocks available that could potentially be used in the above Scheme. A large proportion of these could be derivatised to produce the initial resin-bound intermediate in Scheme 5. Thus there are potentially 200$^2$=40 000 R1'/R2' variations, together with a virtually unlimited combination of R/Y/Z. Even with the 2-hydroxyl acyl transfer mechanism, certain combinations may be too hindered to be practical. However, greater than 80%, i.e. >32000 will be readily accessible using the new system defined in Scheme 4. The limited applicability of the only currently described backbone amide linker system (Scheme 3) is clearly illustrated here. In comparison to Scheme 4 (according to the invention), Scheme 3 (prior art) would have a practical performance capability in only approximately 10%, i.e. 4000 of all allowable R1'/R2' combinations.

EXAMPLES

Libraries of compounds have been synthesised using the novel solid phase combinatorial chemistry of the present invention. Examples are:

Example 1

Libraries of compounds of general formula (H)

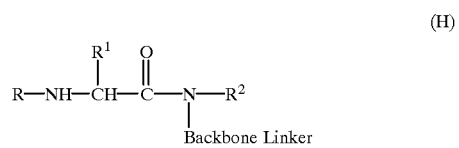

Backbone Linker wherein R$^2$ is selected from the group:

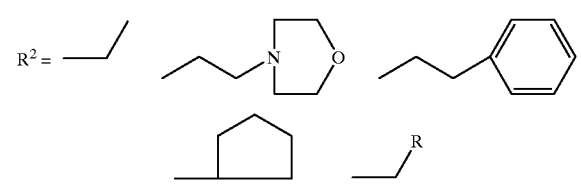

or another primary amine moiety and wherein R1 is combinatorially variable.

These libraries may be useful for discovery of protease inhibitors; for example they may be useful for discovery of Aspartyl protease inhibitor.

Example 2

Libraries of Statine containing compounds of general formula (J)

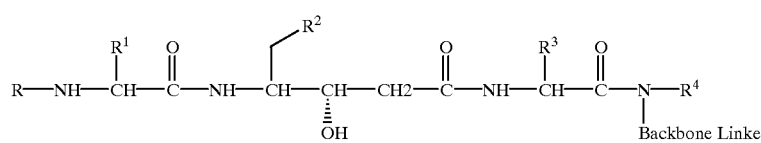

wherein one or both of R1 and $R^4$ are combinatorially variable.

Example 3

Libraries of diketopiperizine compounds of general formula (K) wherein (K) is an intermediate formed by removal of an N-terminal protecting group from a precursor moiety, and wherein K is unstable and hence automatically cyclises:

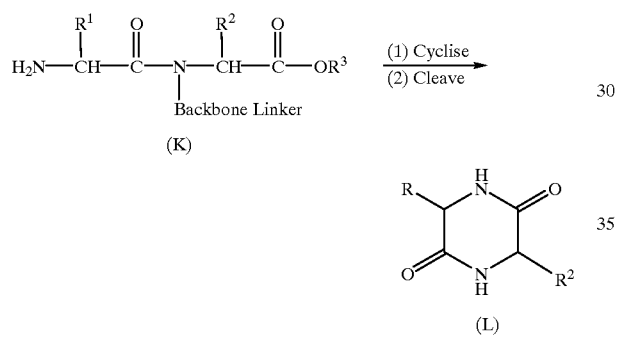

wherein R1 and/or R2 are combinatorially variable, and $R^3$ is an alkyl or allyl leaving group. These compounds (J) are cleavable to form cyclic compounds of general formula (L).

Example 4

Libraries of compounds of general formula (M)

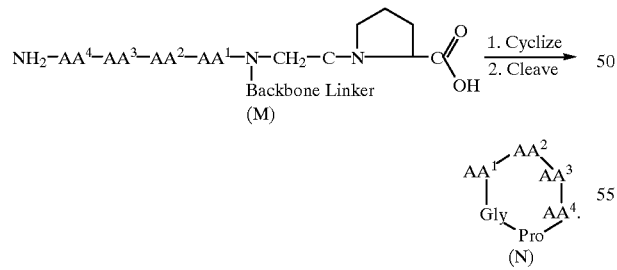

which can be cyclised and cleaved to provide cyclic compounds of general formula A in which $AA^1$–$AA^4$ are independently combinatorially variable. It is a particular advantage of the class of compounds (M) that the Cα of proline cannot easily be epimerised in the reaction and hence chiral integrity of the cyclic product can be preserved.

Thus according to a further aspect of the invention there are provided libraries of compounds and individual compounds per se of formula (H) (J) (K) and (M)—whether attached to the Backbone Linker or in cleaved form, together with libraries and individual compounds per se of formula (L) and (N).

What is claimed is:

1. A method for the preparation of a combinatorial chemistry library of compounds of the formula R1—C(=O)—

NH—R2, wherein R1 and R2 are respectively the residues of acyl and amine combinatorial chemistry building blocks, the method comprising acylation of a combinatorial chemistry intermediate of the formula 1A

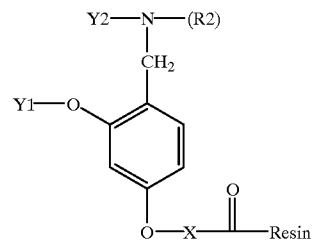

wherein

Y1 is H

Y2 is H or a side chain functional group protecting moiety,

X is selected from the group consisting of

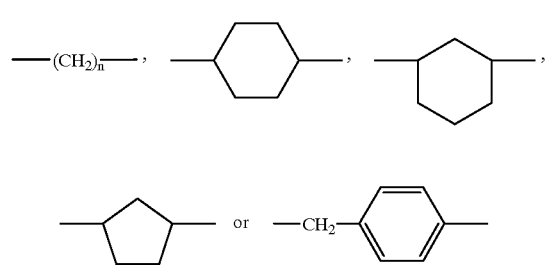

wherein the leftmost bond depicted for each X group is bonded to the —O— of formula 1A and the rightmost bond is bonded to the carbonyl moiety of formula 1A, n is between 2 and 12, R1 and R2 are as defined above, to produce a compound of the formula

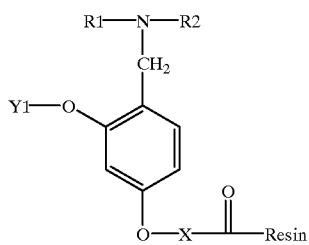

where Y1, R1, R2 and X are as defined above, followed by acidolytic cleavage of the resin bound linker to release said compound of the formula R1—C(=O)—NH—R2.

2. A method according to claim 1 wherein the combinatorial chemistry intermediate of the formula 1A comprises a mixture of individual combinatorial chemistry intermediates wherein the R2 residues on individual intermediates differ.

3. A method according to claim 1 wherein the acylation step uses a mixture of individual R1—C(=O) building blocks, wherein the R1 residues on individual building blocks differ.

4. A method according to claim 1 wherein X is —(CH$_2$)$_n$— and in is 4.

5. A method according to claim 1 wherein the acidolytic cleavage is performed using trifluoroacetic acid, TFA.

6. The method according to claim 1 wherein the Y2 functional group protecting moiety is Fmoc.

* * * * *